(12) United States Patent
Lee et al.

(10) Patent No.: US 9,162,002 B2
(45) Date of Patent: Oct. 20, 2015

(54) CATIONIC FIBERS HOSTING REACTIVE PEROXYGENATED RADICALS, AND METHODS OF MAKING AND USING THEM

(75) Inventors: Kwangyeol Lee, Bellevue, WA (US); Seth Adrian Miller, Englewood, CO (US)

(73) Assignee: Empire Technology Development LLC, Wilmington, DE (US)

( * ) Notice: Subject to any disclaimer, the term of this patent is extended or adjusted under 35 U.S.C. 154(b) by 902 days.

(21) Appl. No.: 13/375,262

(22) PCT Filed: Aug. 19, 2011

(86) PCT No.: PCT/US2011/048412
§ 371 (c)(1),
(2), (4) Date: Nov. 30, 2011

(87) PCT Pub. No.: WO2013/028154
PCT Pub. Date: Feb. 28, 2013

(65) Prior Publication Data
US 2013/0045150 A1 Feb. 21, 2013

(51) Int. Cl.
| | | |
|---|---|---|
| *B01D 53/56* | (2006.01) | |
| *B01J 20/22* | (2006.01) | |
| *A61L 9/00* | (2006.01) | |
| *B01D 39/14* | (2006.01) | |
| *B05D 3/10* | (2006.01) | |
| *C01B 15/08* | (2006.01) | |
| *C02F 1/72* | (2006.01) | |
| *B01D 53/44* | (2006.01) | |
| *A61L 9/01* | (2006.01) | |
| *C02F 1/42* | (2006.01) | |
| *C02F 103/00* | (2006.01) | |

(52) U.S. Cl.
CPC . *A61L 9/00* (2013.01); *B01D 39/14* (2013.01); *B01D 53/44* (2013.01); *B05D 3/10* (2013.01); *C01B 15/08* (2013.01); *C02F 1/72* (2013.01); *C02F 1/722* (2013.01); *A61L 9/01* (2013.01); *B01D 2251/106* (2013.01); *B01D 2253/104* (2013.01); *B01D 2253/34* (2013.01); *B01D 2257/70* (2013.01); *B01D 2257/7027* (2013.01); *C02F 2001/422* (2013.01); *C02F 2103/007* (2013.01); *C02F 2303/04* (2013.01); *C02F 2303/16* (2013.01); *Y10T 428/2933* (2015.01)

(58) Field of Classification Search
CPC .................................. B01D 53/56; B01J 20/22
USPC ................................. 502/400, 401; 423/240 S
See application file for complete search history.

(56) References Cited

U.S. PATENT DOCUMENTS

| | | |
|---|---|---|
| 3,547,580 A | 12/1970 | Cohen |
| 5,824,113 A | 10/1998 | Hojo |
| 7,517,381 B2 | 4/2009 | Rohrbach et al. |
| 8,889,075 B2 | 11/2014 | Tanaka et al. |

FOREIGN PATENT DOCUMENTS

| | | |
|---|---|---|
| CN | 102105403 A | 6/2011 |
| EP | 0687764 A2 | 6/1995 |
| EP | 2199259 A1 | 6/2010 |
| JP | 61202639 A | 9/1986 |
| JP | S61202639 (A) | 9/1986 |
| JP | 2010222739 A | 10/2010 |
| JP | 08209532 A | 6/2011 |
| WO | WO2009/027649 A2 | 3/2009 |
| WO | WO2009041670 A1 | 4/2009 |

OTHER PUBLICATIONS

International Search Report and Written Opinion of PCT/US2011/048412 dated Oct. 17, 2011.
Chowdhury et al., One-pot procedure to synthesize high surface area alumina nanofibers using supercritical carbon dioxide, *Langmuir* (Feb. 16, 2010), 26(4):2707-2713.
Huling et al., In-Situ Chemical Oxidation, *Engineering Issue (United States Environmental Protection Agency)* (Aug. 2006), pp. 1-58.
Root et al., Investigation of Chlorinated Methanes Treatability Using Activated Sodium Persulfate, *Reprint: Proceedings of the First International Conference on Environmental Science and Technology* (2005), pp. 1-6.
Toutianoush et al., Selective transport and incorporation of highly charged metal and metal complex ions in self-assembled polyelectrolyte multilayer membranes, *Materials Science and Engineering* (2002), C 22:135-139.
Redox Tech, LLC, Persulfate, http://redox-tech.com/persulfate1.htm (Printed from Internet Nov. 8, 2011).
Specialty Earth Sciences, LLC, Catalyzed Persulfate Oxidation Treatment—Update, Fort Belvoir Military Garrison (Northern Virginia), (Printed from Internet Nov. 8, 2011).
Fernando et al., Improving an alumina fiber filter membrane for hot gas filtration using an acid phosphate binder, *Journal of Materials Science*, 36 (2001) pp. 5079-5085.
Hori et al., Efficient Decomposition of environmentally Persistent Perfluorocarboxylic Acids by Use of Persulfate as a Photochemical Oxidant, Environ. Sci. Technol., 2005, 39 (7), pp. 2383-2388.

*Primary Examiner* — Edward Johnson
(74) *Attorney, Agent, or Firm* — Pepper Hamilton LLP (57) ABSTRACT

Disclosed are reactive fibers having a polycationic exterior surface to which multivalent peroxy anions are bound. The use of such fibers, mats of such fibers, and filters of such fibers, as well as methods of treating fluid streams, and rejuvenating such fibers, mats and filters are also disclosed.

32 Claims, 4 Drawing Sheets

CATIONIC FIBERS HOSTING REACTIVE PEROXYGENATED RADICALS, AND METHODS OF MAKING AND USING THEM

CLAIM OF PRIORITY

This application is a national phase application under 35 U.S.C. §371 of International Application No. PCT/US2011/048412, filed Aug. 19, 2011, which is incorporated herein by reference in its entirety.

TECHNICAL FIELD

This invention relates generally to fibers, fibrous mats made thereof, and methods of making and using such fibers and fibrous mats. More specifically, the invention relates to cationic fibers hosting reactive moieties, and methods of making and using them.

BACKGROUND

Persulfate is a strong oxidant that has been widely used for initiating emulsion polymerization reactions, clarifying swimming pools, hair bleaching, micro-etching of copper printed circuit boards, and TOC analysis. Among all the persulfate salts typically manufactured (sodium, potassium, and ammonium salts), the sodium form is the most commonly used for environmental applications in the last few years. Sodium persulfate has the potential to in-situ destruct chlorinated and non-chlorinated organic compounds commonly encountered in contaminated soil and groundwater. Other peroxyanions, such as peroxydiphosphate, persilicate, and perborate are also used in bleaching applications.

The persulfate anion ($S_2O_8^{2-}$) and other peroxygenated anions such as peroxydiphosphate, persilicate, etc. can be activated by various methods (heating, UV, transition metal catalysts) to give highly oxidizing radicals. For persulfate, the formed $SO_4^-$ radical has found use in disinfecting water and in removing organic contaminants. Readily available sources of persulfate include $Na_2S_2O_8$, $(NH_4)_2S_2O_8$, $K_2S_2O_8$, etc. These compounds are very soluble in water, and thus when applied to treat a water sample, the radical action is spread over the water's entire volume.

Therefore, in order to treat a large water body, fairly high concentrations of persulfate are required. It has not been possible, to the best of our knowledge, to confine the action of peroxygenated radicals to a desired limited space. Therefore, applications which would benefit from local oxidation, such as filtrations, coatings, etc. (as seen for $TiO_2$ photooxidation systems) have not been possible for peroxygenated anions, even though these oxidants have a distinct advantage over other materials in terms of easy activation.

Accordingly it is desirable to provide a system and method to confine the action of reactive radicals to a limited space, which would enable the fabrication of an effective filter system with oxidizing power for water disinfection and air purification.

SUMMARY

Some embodiments provide a fiber material comprising a fiber defining a positively charged exterior surface, and at least one multivalent peroxy anion bound to the positively charged exterior surface.

Some embodiments provide a fiber mat comprising a plurality of fibers, wherein each of the plurality of fibers comprises a fiber defining a positively charged exterior surface, and at least one multivalent peroxy anion bound by charge-charge interaction to the positively charged exterior surface.

Some embodiments provide a method of purifying a fluid stream, the method comprising the step of contacting the fluid stream with a fiber material comprising a fiber defining a positively charged exterior surface and at least one multivalent peroxy anion to the positively charged exterior surface.

Some embodiments provide a method of making a fiber, the method comprising providing fibers comprising a polycationic exterior surface; contacting the fibers having a polycationic exterior surface with a solution comprising at least one peroxy anion.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Throughout this specification, the terms "peroxy" and "peroxygenated" are used interchangeably and are both consistent with their normal meaning in the art—indicating the presence of an extra oxygen atom, as in peroxides, peroxy acids (e.g., hydrogen peroxide, peroxyformic acid, persulfate, etc.).

In accordance with some embodiments of the invention, a reactive fiber material comprises a fiber having a positively charged exterior surface, to which at least one multivalent peroxy anion is bound.

Multivalent peroxygenated anions such as persulfate ($S_2O_8^{2-}$) are confined on the surface of polycationic fibers, where they will perform as local oxidants. The resultant reactive fiber material is prepared using an ion exchange reaction, when the cationic fibers are washed with a solution containing the multivalent peroxy anion (e.g. $S_2O_8^{2-}$). The peroxygenated anions are confined by electrostatic attraction to the fiber surface until they are decomposed into monoanion radicals (e.g., $SO_4^-$), thus giving the fiber potent oxidizing power. This approach is advantageous because, among other reasons, the activation of persulfate anion, for example, does not require light, allowing the reactive fiber to be used in a variety of water conditions. For example, the described fiber can be fabricated into a filter system for the treatment of a large volume of water with diffuse pollutants. Furthermore, the spent cationic fiber can be rejuvenated with a new set of $S_2O_8^{2-}$ anions by repeating the ion exchange, allowing the reactive filter to be reused.

The fiber used can have a polycationic exterior surface to provide a binding point for the peroxy anions that give the reactive fiber material its strong oxidizing power. This may be naturally occurring based on choice of material or may be achieved via surface modification, such as by coating. Suitable fibers include polycationic salts or fibers that are otherwise polycationic at their outer surface.

In order to confine the multivalent peroxy anions (e.g. persulfate) to a limited space, a fiber that is cationic in aqueous systems, such as alumina, ceria or zirconia may be used. Additionally, fibers such as carbon fiber, zinc oxide, nickel oxide, may be used. The fibers may be used alone or in combination with one another. Fibers made from such materials naturally or inherently provide a polycationic exterior surface. In some embodiments, inorganic fibers are preferred.

Alternatively, in some uses a neutral or anionic fiber (e.g., silica, inorganic/organic composites, cellulose driven carbon fiber, carbon nanotube, exfoliated graphene, titania, tin oxide, etc.) may be coated with a cationic polymer to impart a positive charge to its surface. Suitable polymer coatings include but are not limited to poly(ethyleneimine), poly(diallyldimethylammonium chloride) and combinations thereof. Biological polymers such as chitosan, collagen, wool, etc. may also be used. Poly(ethyleneimine) or poly(diallyldimethylammonium chloride) are both excellent choices as polycations, and can be coated onto a fiber by dip coating, or other process, to make the surface of the selected fiber or fibers positively charged even if it possesses a native uncharged or negatively charged state. In some embodiments, a mat or filter of a plurality of fibers may be coated together, rather than coating individual fibers before assembling the mat or filter.

In some instances, a base fiber can be treated to make it anionic. For example, the fiber could be oxidized under a flow of ozone or via an oxygen plasma, which would result in a large density of carboxylates, which will be anionic at pH>5. Sulfination techniques may also be employed to create sulfate groups on the fiber to create the polyanion. This may be preferable at larger scales, while the gas phase treatment may be preferred at smaller scales.

To make the fibers reactive (e.g. oxidizing), the fibers can be dipped into a solution of the peroxygenated anion. Suitable multivalent peroxygenated anions include but cannot limited to persulfate ($S_2O_8^{2-}$), peroxydiphosphate ($P_2O_8^{4-}$), persilicate ($SiO_4^{2-}$), or perborate ($B_2O_4(OH)_4^{2-}$). Their source may be a solution of compounds containing them such as their salts. Particularly potassium salts, sodium salts and ammonium salts may be used (e.g., $Na_2S_2O_8$). Persulfate is recited in much of the discussion herein, however, please note that any of the multivalent peroxygenated anions will work; each having its own advantages. The multivalent peroxy anion may be a di-anion, a tri-anion, or a tetra-anion, or combinations thereof. Without being bound by theory, it is believed that because these oxidizing anions are typically di- or tetra-anions, they will immediately displace any monoanions on the fiber surface, and remain there even if the surface is washed. This procedure can be accomplished in a single step on individual fibers, or over the surface of a collection of fibers, for example in a pre-fabricated membrane, mat or filter. The volume of solvent required to make a given amount of fiber reactive will depend on things like the fiber shape, volumetric packing density, etc. In some examples, about 100 mL of persulfate solution will treat 1 g of fibers, depending on the fiber source. In a fiber mat, it is contemplated that about 10 mL of persulfate will treat a 49 mm diameter filter having a thickness of about 300 μm. More or less may be required in different situations, with different fibers, new filters, or spent filters.

The ability to displace the monoanions allows for quick and easy rejuvenation of the fibers, by simply contacting a spent fiber with a fresh source of multivalent peroxygenated anions.

The surface confined multivalent peroxy anions can be activated by various routes (UV, heat, transition metal ions) to provide oxidizing agents in the form of reactive radicals (e.g. $SO_4^-$ radicals) which can oxidize organic contaminants in fluid streams such as water and gas. Thus, a fluid stream in contact with such fibers places organic contaminants in contact with activated reactive fibers. The contaminants are oxidized through the strong oxidizing power of the now activated peroxy radicals. In this manner, the fluid stream is treated to remove at least a portion of the organic contaminants present in the fluid stream. The list of organic contaminants that may be treated includes, but is not limited to aromatic organic compounds, polychlorobiphenyls, benzene, toluene, ethylbenzene, xylene, 1,1,dichloroethane, 1,2-dichlorobenzene, 1,3-dichlorobenzene, vinylchloride, methylenechloride, chloroform, aldrin, chlordane, DDT, dieldrin, endrin, heptachlor, hexachlorobenzene, mirex, polychlorinated biphenyls, polychlorinated dibenzo-p-dioxins, polychlorinated dibenzofurans, and toxaphene and combinations thereof.

The reactive fiber material can be created by dip-coating a cationic fiber in a solution of peroxygenated anions. Treatment can be performed at the fibers, where the oxidizing agents are released locally during an activation step. Once the oxidizing agent in the fiber is spent, the fibers can be rejuvenated by dip-coating them again. The reaction is generically depicted below. It should be readily understood that the treatment step involving contacting the fluid stream with the fiber material occurs between activation and rejuvenation.

Figure 1A:
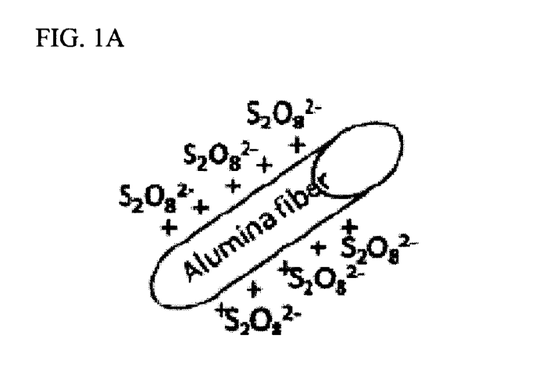
FIG. 1A shows a cross-sectional perspective view of a fiber material.
Figure 1B:
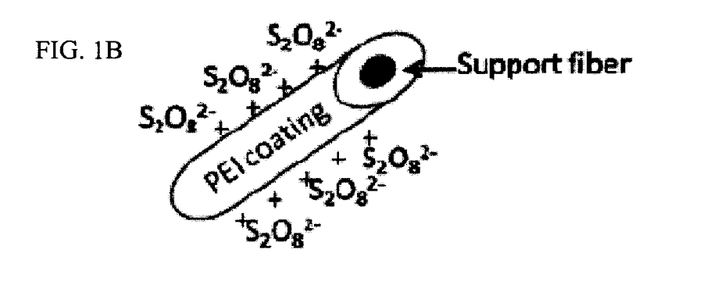
FIG. 1B shows a cross-sectional perspective view of a fiber material.
Figure 2:
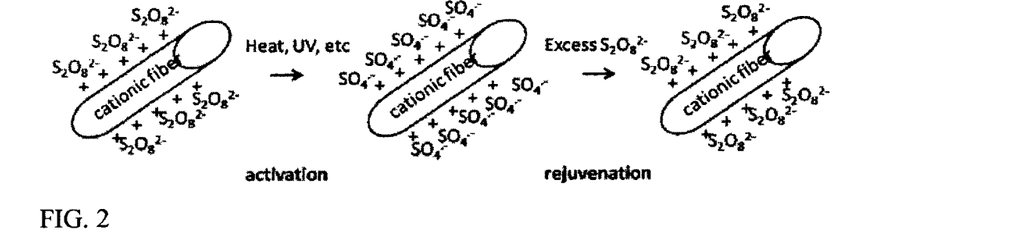
FIG. 2 depicts the activation and rejuvenation reactions of a fiber material.
Figure 3A:
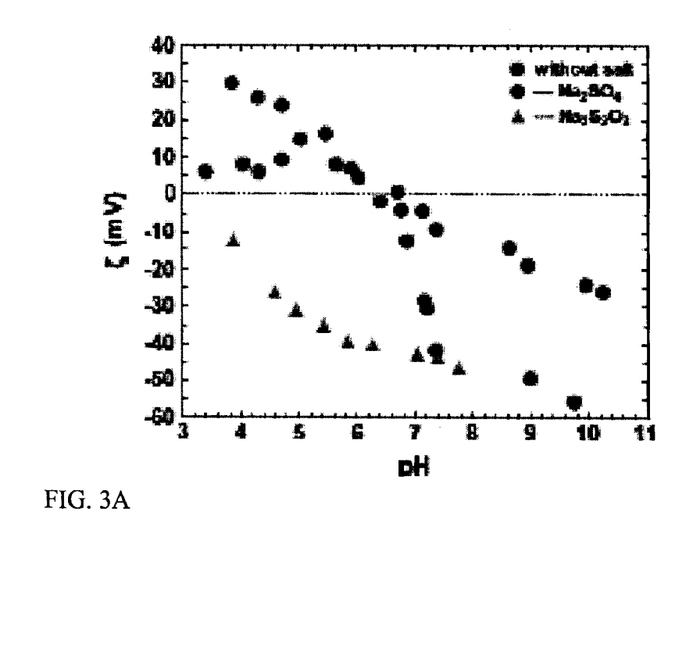
FIGS. 3A and 3B include two comparative graphs, showing (a) the relative attractions of dianions and (b) monoanions on alumina.
Figure 3B:
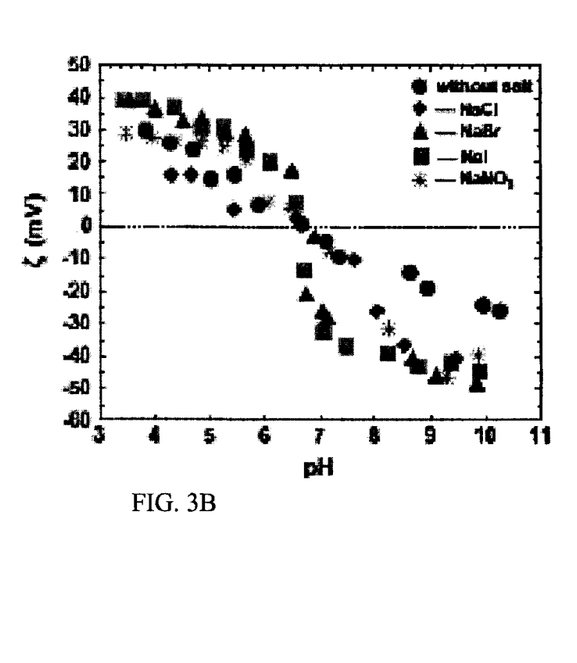

Alumina is structurally robust and easily fabricated into a desired filter system and therefore a good choice for the polycationic fiber. Alumina is cationic in acidic and neutral pHs (pKa=7-9). Advantageously, alumina also does not readily degrade when in contact with an oxidant. As shown in FIG. 3, the zeta potential of alumina is positive under neutral and acidic conditions, but when dianions are added they strongly absorb to the surface, leading to either cancellation of the charge (in the case of sulfate) or even charge reversal (in the case of $S_2O_3$). Addition of sulfate dianions completely neutralizes the surface, and $S_2O_3$ dianions bind so tightly that they impart a net negative charge to the surface, as evidenced in FIG. 3a. By comparison, as shown in FIG. 3b, monoanions do not bind nearly as tightly, as evidenced by their far smaller effect on the zeta potential. The greater binding of the multivalent peroxy anions can be leveraged to displace the monoanions to recharge a spent fiber. The synthesis of alumina fiber with very high surface areas that will accommodate large amounts of peroxygenated anions has been previously described. As the peroxygenated anions are spent, a monoanion may be left bound to the fiber. By contacting the spent fiber with fresh multivalent peroxygenated anion, the monoanion is displaced, and the fiber is recharged. It is believed that other naturally cationic fibers will exhibit similar properties.

Other non-cationic fibers can be rendered cationic on their surfaces by treatment with an appropriate polycationic material, such as polycationic polymers. PEI (poly ethylene imine) can be protonated and therefore can possess numerous cationic centers at about pH 9 or less. Such coatings are appropriate for applications with weaker oxidants such as persilicates, as they may be destroyed by harsher oxidants such as persulfate. Because PEI and other polycations can be coated as a single layer by dip coating, it is easy to restore this coating after use if necessary.

As stated above, multivalent peroxy anions (e.g. persulfate) can be activated by various means to give reactive radicals (e.g. $SO_4^-$). For example, a filter made from the reactive fiber can be heated, irradiated by UV, or treated with transition metal complexes such as $FeSO_4$, $FeCl_2$, etc. to accelerate production of active radicals. Heating may be to generally any temperature sufficient to activate the anions. Example temperatures include about 20° C., about 30° C., about 40° C., about 50° C., about 80° C., about 90° C. and ranges between any two of these values. For example, the methods and apparatus described herein could be employed in wastewater streams in applications such as textile dyeing which can be at temperatures of about 80-90° C. If desired, heating may be performed using resistive wires embedded in a filter made up of the reactive fibers, so that the heating takes place locally at the filter itself, saving tremendously on energy compared to heating up the entire solution to be treated. A used (or spent) filter or fiber can be regenerated by introducing an aqueous solution containing multivalent peroxy anions (e.g. persulfate anions). The concept of online regeneration of the filter system is shown the schematic shown in FIG. 6. Accordingly, regeneration of a cationic filter with additional multivalent peroxy anions (e.g. persulfate) can be performed in situ without any special handling of the filter.

Figure 4:
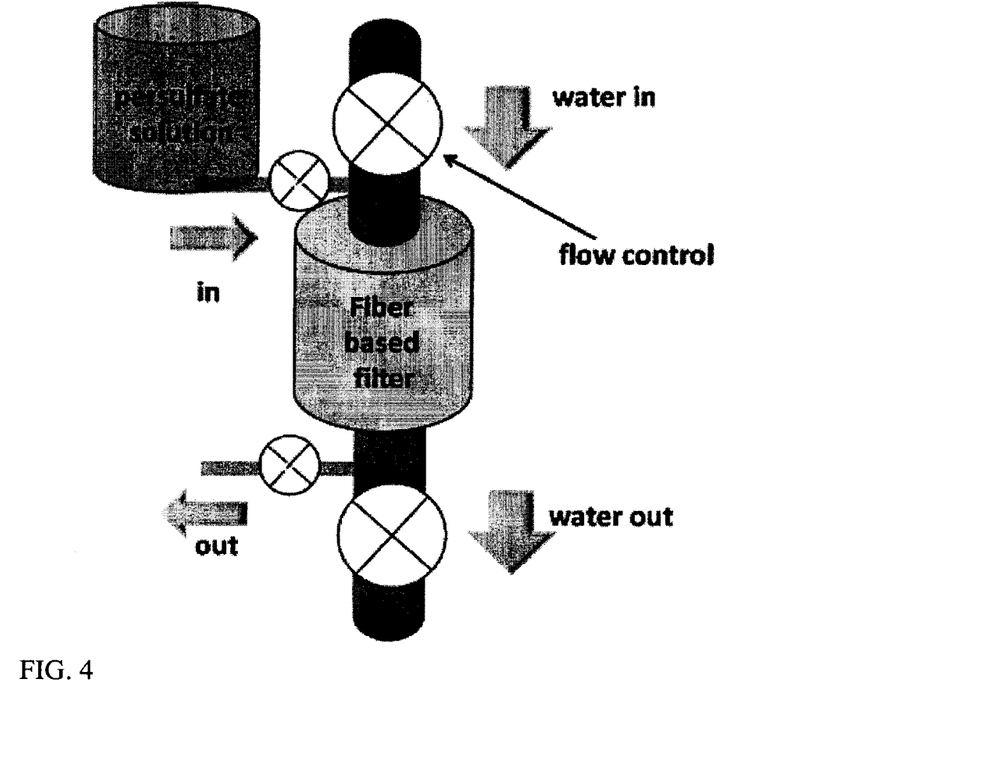
FIG. 4 depicts the flow in a water treatment system, including in situ regeneration of a cationic filter in accordance with some embodiments of the invention.

As depicted, in FIG. 4, during treatment, a filter or fibrous mat made up of the reactive fiber material described herein is provided for contact with the fluid stream to be treated. The filter maybe have been previously activated or activated in situ, to provide reactive radicals at the surface of the reactive fiber material. The fluid stream is then allowed to flow, making contact with the reactive fiber material, thereby reacting with and oxidizing at least a portion of the organic contaminants within the fluid stream. Once the desired treatment has been achieved, or the reactive potential of the filter has been met, the filter may be rejuvenated. Through manipulation of suitable valves and conduits in the system, a solution containing multivalent peroxy anions is passed over and through the filter. Upon such contact, the multivalent peroxy anions displace the spent monovalent anions resulting in a rejuvenated filter containing reactive fiber material which may be used to treat additional fluid streams. This cycle may be repeated multiple times.

Other materials beyond persulfate may be used as the peroxy anion. Persulfate can be used in instances where its extremely high oxidizing power (Ev=2.7 V) is desirable. However, it will not always be compatible with coated organic fibers, as it may oxidize organics in the fiber itself. Therefore, other oxidants may sometimes be selected. Peroxydiphosphate may be chosen because it is a tetraanion, and thus will bind more tightly to the polycation surface (until broken down by a heat, light, or chemical trigger), and may be desirable for use with extremely dilute solutions. Peroxydiphosphate compounds have been known for over 80 years, and have been used in commercial applications such as hair bleaching. It has oxidizing power (Ev=2.07 V) greater than that of ozone, and is therefore an excellent choice for this application.

Other peroxy anions include persilicate and perborate, milder dianions which may find use in specific applications where organic filter materials are desired.

In traditional systems, an oxidizing agent is not fabricated as part of the filter, or must be shipped wet with the filter. As described herein, however, the multivalent peroxy anion is bound strongly as part of the reactive fiber material that makes up a filter or fiber mat. Such a filter or mat can be stored and shipped dry in an unactivated state. The filter may be activated once on site. Once activated, the monovalent radical (e.g. $SO_4^-$) has an oxidation potential greater than ozone (and almost as high as hydroxyl radicals), yet as discussed herein, is confined to the fiber surface which is well-suited for on-site treatment of large volumes of water or other fluids. Activation, in some cases, requires only mild heating, which can optionally be provided by an embedded resistive heater. Therefore, deep and dark water can be treated, an advantage over UV or light based filters. One advantage of the system lies in the fact that nothing unnecessary goes into the body of water being treated.

The activity of the filter can be regenerated by a reaction with persulfate anions. The filter system can be regenerated by online treatment, which is a great advantage over other nonreusable reactive filter systems.

The reactive fibers described herein may be assembled into fiber mats or filters by techniques well known in the art. One simple method is to form a slurry of fibers and filter them to make a fiber mat. The fiber may be random or oriented in a particular pattern, depending upon the application. Other methods such as casting the slurry onto a web may be used. If the fibers have a sufficiently high aspect ratio, they become entangled. Otherwise, you can add a small amount of binder to hold them together.

Importantly, the fiber mats or filters can be made from fibers before reaction with the multivalent peroxy anion or, the mat or filter may be formed first and then reacted with the multivalent peroxy anions. Either way, the net result is a mat or filter that is reactive by virtue of the multivalent peroxy anions bound to the outer surface thereof.

The description above, and the examples below are meant to be illustrative in nature and are not intended to limit the scope of the invention.

EXAMPLES

Example 1

Preparation of an Alumina Persulfate Fiber

A reactive fiber material can be made by mixing a quantity of alumina fibers (commercially available) with a solution containing persulfate anions from a persulfate salt (0.001 mM to 1M) at about 20° C. to about 30° C. for 1 minute to about 1-15 minutes. The resultant fibers are then separated from the liquid to yield reactive fibers having persulfate bound to their exterior surface.

| Cationic Fiber | g | Persulfate salt | mL | Concentration |
|---|---|---|---|---|
| Alumina | 1 | $Na_2S_2O_8$ | 100 | 0.001 mM-1M |
| Alumina | 1 | $K_2S_2O_8$ | 100 | 0.001 mM-1M |
| Alumina | 1 | $(NH_4)_2K_2SO_8$ | 100 | 0.001 mM-1M |

Example 2

Preparation of a Ceria Persulfate Fiber

A reactive fiber material is made by mixing a quantity of ceria fibers (commercially available) with a solution containing persulfate anions from a persulfate salt (about 0.001 mM-about 1M) at about 20° C. to about 30° C. for 1 minute to about 1 to about 15 minutes. The resultant fibers are then separated from the liquid to yield a plurality of reactive fibers having persulfate bound to their exterior surface.

| Cationic Fiber | Persulfate salt | Concentration |
| --- | --- | --- |
| Ceria | $Na_2S_2O_8$ | 0.001 mM-1M |
| Ceria | $K_2S_2O_8$ | 0.001 mM-1M |
| Ceria | $(NH_4)_2K_2SO_8$ | 0.001 mM-1M |

Example 3

Preparation of a Reactive Persulfate Fiber from a Fiber Having a Polymeric Coating A reactive fiber material is made by mixing a quantity of fibers (these may be cationic, anionic, or neutral) with a polycationic polymer material such that all or a portion of the fiber is coated with the polycationic polymer material to yield a coated fiber having a polycationic exterior surface.

| Fiber | Polymer |
| --- | --- |
| cationic, anionic, or neutral | Poly(ethylenimine) |
| cationic, anionic, or neutral | 1% Poly(diallyldimethylammonium chloride) |

Mixing a quantity of the coated fibers with a solution containing peroxydiphosphate anions from a persulfate salt at about 20° C. to about 30° C. for 1 minute to about 24 hours. The resultant fibers are then separated from the liquid to yield reactive fibers having persulfate bound to their exterior surface.

Example 4

Preparation of Mat From Reactive Fiber Material

A mat of reactive fiber material is formed through traditional non-woven techniques, such as dry laying or wet laying. To make such mats, a quantity of alumina persulfate fiber material is deposited on a surface via dry-laying techniques until a mat of desired size and thickness is formed. The mat is then removed from the surface for use. The mat may be made or cut to desired size.

Example 5

Preparation of a Mat from a Fiber Material with Subsequent Addition of Reactive Coating A filter mat is prepared via non-woven techniques from a polycationic fiber material and subsequently coated with a peroxyanion.

A quantity of alumina fibers are dry laid to form a fibrous mat of desired size and thickness. For example, a filter mat having a 49 mm diameter and thickness of about 300 μm can be made through dry-laying techniques. The fibrous mat is then contacted with a solution of $Na_2S_2O_8$. About 10 mL of a 100 mM solution of $Na_2S_2O_8$ is used to produce an alumina fiber mat coated with persulfate.

Example 6

Polymer Coated Resin Filter Mat

A flow of ozone or a downstream oxygen plasma oxidizes the surface of a conventional hydrophobic polymer fiber (or filter), such as polypropylene to create a large density of carboxylates, which will be anionic at pH≥5. The oxidized polypropylene then exposed to a solution of polyethyleneimine (0.1 M) for 1-15 minutes. As above, a 49 mm filter may require about 10 mL of fluid.

Example 7

Treatment of Lakes and Streams

In a typical application, slurried fibers are dried into sheets using a small amount of a binder such as a polyacrylate, so that the sheets are approximately 300 μm thick. These sheets are wound into spiral filter modules used for water treatment.

To charge or recharge the filter, a solution of 0.5-1M peroxyanion is passed through the filter. This outcompetes the existing anions and replaces them with the desired oxidants. The spiral filter may then be placed in a fluid flow for treatment of the water passing therethrough.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A fiber material comprising:
a fiber defining a positively charged exterior surface;
at least one multivalent peroxy anion bound to the positively charged exterior surface.

2. The fiber material of claim 1, wherein the at least one multivalent peroxy anion is bound via charge-card interaction.

3. The fiber material of claim 1, wherein the fiber itself is positively charged, thus providing the positively charged exterior surface.

4. The fiber material of claim 1, wherein the fiber is an inorganic fiber that is cationic in aqueous solution.

5. The fiber material of claim 1, wherein the fiber is selected from carbon nanotube, cellulose, carbon fiber, zinc oxide, nickel oxide, alumina, ceria and combinations thereof.

6. The fiber material of claim 1, wherein the positively charged exterior surface comprises a polycationic polymer coating on the fiber.

7. The fiber material of claim 6, wherein the fiber is at least partially coated with a polycationic polymer to provide a positively charged exterior surface to the fiber.

8. The fiber material of claim 6, wherein the positively charged exterior surface comprises a polycationic polymer at least partially coating the fiber.

9. The fiber material of claim 6, wherein the polycationic polymer is selected from poly(ethyleneimine), poly(diallyldimethylammonium chloride) polyacrylamide, high molecular weight quaternary amines, biological polymers, and combinations thereof.

10. The fiber material of claim 1, wherein the fiber defining a positively charged exterior surface comprises a negative or neutral fiber at least partially coated with a cationic polymer.

11. The fiber material of claim 1, wherein the fiber comprises a natural polycationic exterior surface in an aqueous solution and the peroxy anion is selected from persulfate ($S_2O_8^{2-}$), peroxydiphosphate ($P_2O_8^{4-}$), persilicate ($SiO_4^{2-}$), perborate ($B_2O_4(OH)_4^{2-}$), and combinations thereof.

12. The fiber material of claim 1, wherein the fiber comprises a natural polycationic exterior surface in an aqueous solution and the peroxy anion is selected from persulfate ($S_2O_8^{2-}$), peroxydiphosphate ($P_2O_8^{4-}$), persilicate ($SiO_4^{2-}$), perborate ($B_2O_4(OH)_4^{2-}$), and combinations thereof.

13. The fiber material of claim 1, wherein the fiber is selected from alumina, ceria and combinations thereof and the peroxy anion is selected from persulfate ($S_2O_8^{2-}$), peroxydiphosphate ($P_2O_8^{4-}$), persilicate ($S_2O_8^{2-}$), perborate ($B_2O_4(OH)_4^{2-}$), and combinations thereof.

14. The fiber material of claim 1, wherein the fiber is alumina and the peroxy anion is persulfate.

15. The fiber material of claim 1, wherein the fiber is at least partially coated with a polycationic polymer and the peroxy anion is persilicate.

16. A fiber mat comprising:
a plurality of fibers, wherein each of the plurality of fibers comprises a fiber defining a positively charged exterior surface, and at least one multivalent peroxy anion bound by charge-charge interaction to the positively charged exterior surface.

17. The fiber mat of claim 15, wherein the at least one multivalent peroxy anion is bound via charge-charge interaction.

18. A method of purifying a fluid stream, the method comprising:
contacting the fluid stream with a fiber material comprising a fiber defining a positively charged exterior surface and at least one multivalent peroxy anion bound to the positively charged exterior surface.

19. The method of claim 18, wherein the at least one multivalent peroxy anion is bound via charge-card interaction.

20. The method of claim 18, wherein the fluid stream is gas or liquid.

21. The method of claim 18, wherein the at least one multivalent peroxy anion is activated by UV, heat, reaction with transition metal ions, or combinations thereof, prior to the contacting step.

22. The method of claim 18, wherein the fluid stream comprises at least one organic contaminant to be removed from the fluid stream.

23. The method of claim 18, wherein the at least one organic contaminant comprises benzene, toluene, ethylbenzene, xylene, 1,1,dichloroethane 1,2-dichlorobenzene, 1,3-dichlorobenzene, vinylchloride, methylenechloride, chloroform, aldrin, chlordane, DDT, dieldrin, endrin, heptachlor, hexachlorobenzene, mirex, polychlorinated biphenyls, polychlorinated dibenzo-p-dioxins, polychlorinated dibensofurnas, and toxaphene and combinations thereof.

24. The method of claim 18, further comprising
regenerating the bound multivalent peroxy anions on a fiber, after contact with the fluid stream, by contacting the fiber with an aqueous solution containing the multivalent peroxy anions.

25. The method of claim 18, wherein the fiber comprises alumina and the multivalent peroxy anion comprises persulfate.

26. A method of making a fiber, the method comprising:
providing fibers comprising a polycationic exterior surface;
contacting the fibers having a polycationic exterior surface with a solution comprising at least one peroxy anion.

27. The method of claim 25, wherein providing the fiber comprises the step of at least partially coating a fiber with a polymer that is polycationic in aqueous solution.

28. The method of claim 25, wherein the polycationic polymer is selected from poly(ethyleneimine), poly(diallyldimethylammonium chloride), polyacrylamide, high molecular weight quaternary amines, biological polymers, and combinations thereof.

29. The method of claim 26, wherein the fiber is selected from carbon nanotube, cellulose, carbon fiber, zinc oxide, nickel oxide, alumina, ceria and combinations thereof.

30. The method of claim 25, wherein the at least one peroxy anion is selected from persulfate ($S_2O_8^{2-}$), peroxydiphosphate ($P_2O_8^{4-}$), persilicate ($SiO_4^{2-}$), perborate ($B_2O_4(OH)_4^{2-}$), and combinations thereof.

31. The method of claim 25, wherein the fiber is alumina and the peroxy anion is persulfate.

32. The method of claim 25, wherein the fiber is at least partially coated with a polycationic polymer and the peroxy anion is persilicate.

* * * * *